United States Patent
Fang et al.

(10) Patent No.: US 9,697,333 B2
(45) Date of Patent: Jul. 4, 2017

(54) AUDIBLE BARCODE SYSTEM AND METHOD

(71) Applicant: SafeNet International LLC, Arlington Heights, IL (US)

(72) Inventors: Joseph Y. Fang, South Barrington, IL (US); Jindong Liu, Chiba (JP)

(73) Assignee: SAFENET INTERNATIONAL LLC, Arlington Heights, IL (US)

( * ) Notice: Subject to any disclaimer, the term of this patent is extended or adjusted under 35 U.S.C. 154(b) by 0 days.

(21) Appl. No.: 15/134,532

(22) Filed: Apr. 21, 2016

(65) Prior Publication Data

US 2016/0314271 A1    Oct. 27, 2016

Related U.S. Application Data

(60) Provisional application No. 62/151,406, filed on Apr. 23, 2015.

(51) Int. Cl.
    *G06K 7/10*         (2006.01)
    *G06F 7/00*         (2006.01)
    *G06F 19/00*       (2011.01)

(52) U.S. Cl.
    CPC ................ *G06F 19/3456* (2013.01)

(58) Field of Classification Search
    USPC ........................................ 235/375, 462.01
    See application file for complete search history.

(56) References Cited

U.S. PATENT DOCUMENTS

| | | | |
|---|---|---|---|
| 8,538,064 B2 | 9/2013 | Rhoads et al. | |
| 8,550,354 B2 | 10/2013 | Gannon et al. | |
| 8,602,309 B2 | 12/2013 | Longacre, Jr. et al. | |
| 8,657,189 B2 | 2/2014 | Berkun | |
| 2012/0085829 A1* | 4/2012 | Ziegler | G09F 3/14 235/493 |
| 2013/0066633 A1 | 3/2013 | Krishnan | |
| 2013/0334300 A1 | 12/2013 | Evans | |
| 2014/0325328 A1 | 10/2014 | Beadles | |
| 2014/0339296 A1 | 11/2014 | McAdams et al. | |
| 2015/0008257 A1 | 1/2015 | Beadles | |
| 2015/0028104 A1 | 1/2015 | Ma et al. | |
| 2015/0102098 A1* | 4/2015 | Adams | H04L 67/1097 235/375 |
| 2015/0142144 A1 | 5/2015 | Damir et al. | |

\* cited by examiner

*Primary Examiner* — Daniel Hess
(74) *Attorney, Agent, or Firm* — Bishop Diehl & Lee, Ltd.

(57) ABSTRACT

A system and method using a mobile Internet device with ability to scan a barcode in which a uniform resource locator (URL) is placed, and plays a transmitted audio signal activated by the URL in a Cloud database where both audio and word contents are stored. From general information for direction, instruction and information on the bottle of medicine, nutrition facts and ingredient tables on the packages of food, monthly bills, invoices, menu, magazines, to advertisement—all are either possessed of limited language translation options or use small font to explain something in a limited space. The system and method provide translation options and an audible signal.

9 Claims, 4 Drawing Sheets

(EDITING PROCEDURES TO BUILD LINKS BETWEEN TEXT CONTENTS AND AUDIO)

(AEGISUB'S APPLICATION TO CREATE AND MODIFY SUBTITLES TO AUDIO)

URL
Http://www.q-sl.com/kk/f?p=E2
|←1→| |←—2—→| |←-3-→||4|

(LAYOUT OF TEXT CONTENTS AND 2D BARCODE)

| POT | TL | START | END | L Left | L Vert | R Left | R Vert | English |
|---|---|---|---|---|---|---|---|---|
| E1 | 4 | 0:22:15 | 0:22:18 | 1 | 1 | 51 | 1 | Metformin is a medicine used in diabetes mellitus |
| | | 0:22:19 | 0:22:21 | 53 | 1 | 13 | 3 | The information in this Medicine Guide for metformin hydrochloride |
| | | 0:22:21 | 0:22:25 | 15 | 3 | 50 | 4 | varies according to the condition being treated and the particular preparation used. |
| | | 0:22:26 | 0:22:29 | 1 | 5 | 43 | 5 | Take 1 tablet by mouth every day with meal. |

*Fig. 4*

(EXAMPLE OF TIME SEQUENCE AND TEXT CONTEXT ASSOCIATED TOGETHER AND INDEXED)

(EDITING PROCEDURES TO BUILD LINKS BETWEEN TEXT CONTENTS AND AUDIO)

AUDIBLE BARCODE SYSTEM AND METHOD

RELATED APPLICATION

This application claims the filing priority of U.S. Provisional Application No. 62/151,406 titled "A Method Uses 2D Barcode to Quickly Sort in Cloud Database and Listen Transmitted Audio in Mobile Internet Devices" and filed on Apr. 22, 2015. The '406 application is hereby incorporated by reference.

TECHNICAL FIELD OF INVENTION

The present invention relates to a system and method for providing audible information through a mobile device using typical barcode labels and a database.

BACKGROUND OF INVENTION

It has long been a problem in the healthcare and medical fields to provide packaging which conveys all the important information about a product to a user. Packaging which is too large can hold considerable information, but is difficult to carry about in a pocket or purse. Conversely, packaging which is small is easier to carry, but provides very limited space for printing valuable information. This problem is of particular concern where over-the-counter (OTC) and prescription medications are involved.

As the required warning labels and use instructions have increased over the years, even large containers could no longer provide adequate space for printing of critical information. In response, some companies have used long labels which fold onto themselves and can be expanded by the consumer to reveal information about a product. The problem with all of these packages is that the print is often too small to read. They also fail to address situations where the reader is unable to read and/or understand the printed information due to a language barrier, an affliction of sight, a reading disorder, or merely as a result of commonly misreading information.

In a seemingly unrelated technology, using a Cloud-based computer and database, there is virtually unlimited space to store static word contents and their continuous audio signals and allow the computing power to effectively and quickly sort and process this data. As a result of this technology, the "mobile Internet" is growing rapidly. In the United States, an estimated 30% of web browsing and 40% of social media use are done on mobile devices such as smartphones and tablets ("Embracing the Internet of everything to capture your share of $14.4 Trillion," by J. Bradley, J. Barbier, and D. Handler, Cisco Systems, Feb. 12, 2013).

Further, it is currently an existing feature to allow 2D barcode scanning by a smartphone for the purpose of identity verification or to receive product information. However, no known technologies or developers are focusing on effectively translating word content on paper to an audio voice (i.e., read to you in real time) using only a simple action without scanning entire subject word contents.

The invention of the present application is designed to address these and other issues faced by the healthcare and medical industries. The disclosed system and method provide a viable alternative for individuals and facilitates proper usage of products, such as OTC and prescription medications, with numerous advantages in simplicity and effectiveness.

SUMMARY OF INVENTION

There is disclosed herein an improved system and method which avoid the disadvantages of prior devices while affording additional structural and operating advantages.

Generally speaking, the disclosed method provides an audio signal to an electronic device via an Internet connection where the audio signal is related to printed information associated with a barcode.

In a specific embodiment, the method comprises the steps of creating text content based on the printed information, recording an audio signal in a first language based on the printed information in a second language, editing the text content into text segments based on meaning, listing the text segments in a table, defining audio segments of the audio signal by start and stop time code sequences of the recording, wherein the audio segments correspond with listed text segments in the table, adding the time code sequences to the table for the text segment based on the corresponding audio segment, adding a location to the table for each text segment in the text content, storing the audio signal and text segments in table format on a cloud-based server, generating a unique URL linked to the stored audio signal and text segments and to a web-based audio play application, generating a barcode containing the URL, and scanning the barcode to activate the audio signal.

Generally, in the disclosed system, an audio signal is provided to an electronic device via an Internet connection where the audio signal is related to printed information associated with a bar code.

In a specific embodiment, the system comprises a container having a product therein and printed instructions thereon associated with the product, a barcode affixed to the container proximate the printed instructions, wherein the barcode comprises a URL which links to a server having an audio signal corresponding to the printed instructions stored thereon, a scanning device having an Internet connection for reading the barcode, following the URL link to the server, and activating the stored audio signal, and a speaker coupled to the scanning device for playing the audio signal.

With a smartphone or Internet devices (such as Medical Pendant), people are able to scan a 2D barcode and listen the contents printed at a small area with a small font otherwise have to use prescribed glass or magnified glass with proper lighting, as long as there is a 2D barcode at the next print area. It can be applied as translator to overcome language barrier in different language environment.

These and other features, elements, functions, benefits and uses for the disclosed system and methods will be more understood the detailed description given herein below and the accompanying drawings.

BRIEF DESCRIPTION OF DRAWING

For the purpose of facilitating an understanding of the subject matter sought to be protected, there are illustrated embodiments thereof, from an inspection of which, when considered in connection with the following description, the subject matter sought to be protected, its construction and operation, and many of its advantages should be readily understood and appreciated.

FIG. 4 is a table in illustrating text in a document segmented according to meaning and associated with an audio time sequences.

DETAILED DESCRIPTION OF A PREFERRED EMBODIMENT

While this invention is susceptible of embodiments in many different forms, there is shown in the illustrations and will herein be described in detail at least one preferred embodiment of the invention with the understanding that the present disclosure is to be considered as an exemplification of the principles of the invention and is not intended to limit the broad aspect of the invention to any of the specific embodiments illustrated or described.

Generally speaking, with reference to FIGS. 1-5, the present system and methods comprise use of 2D barcodes, a database and a mobile device to provide audio related to product information to a user. Preferably, the barcode is applied to a label having critical use information for a medical product, including but not limited to OTC drugs, prescription medication, dietary supplements, vitamins, and the like. The 2D barcodes store a URL (see FIG. 2) and quickly sort continuous Audio signals to match the word contents in the Cloud and transmit it to mobile device (e.g., a medical pendant). The mobile device is then able to convey the word contents to the user.

Preferably, the audible content is related to "instructions for use" on a bottle for a medical product (see FIG. 3) and is activated by scanning the 2D barcode with a single click (like taking a picture). With the user's personal information carried in the smart device, the URL can be assembled with language indices so that a translation context can be read according to the user's preferred language.

Figure 1:
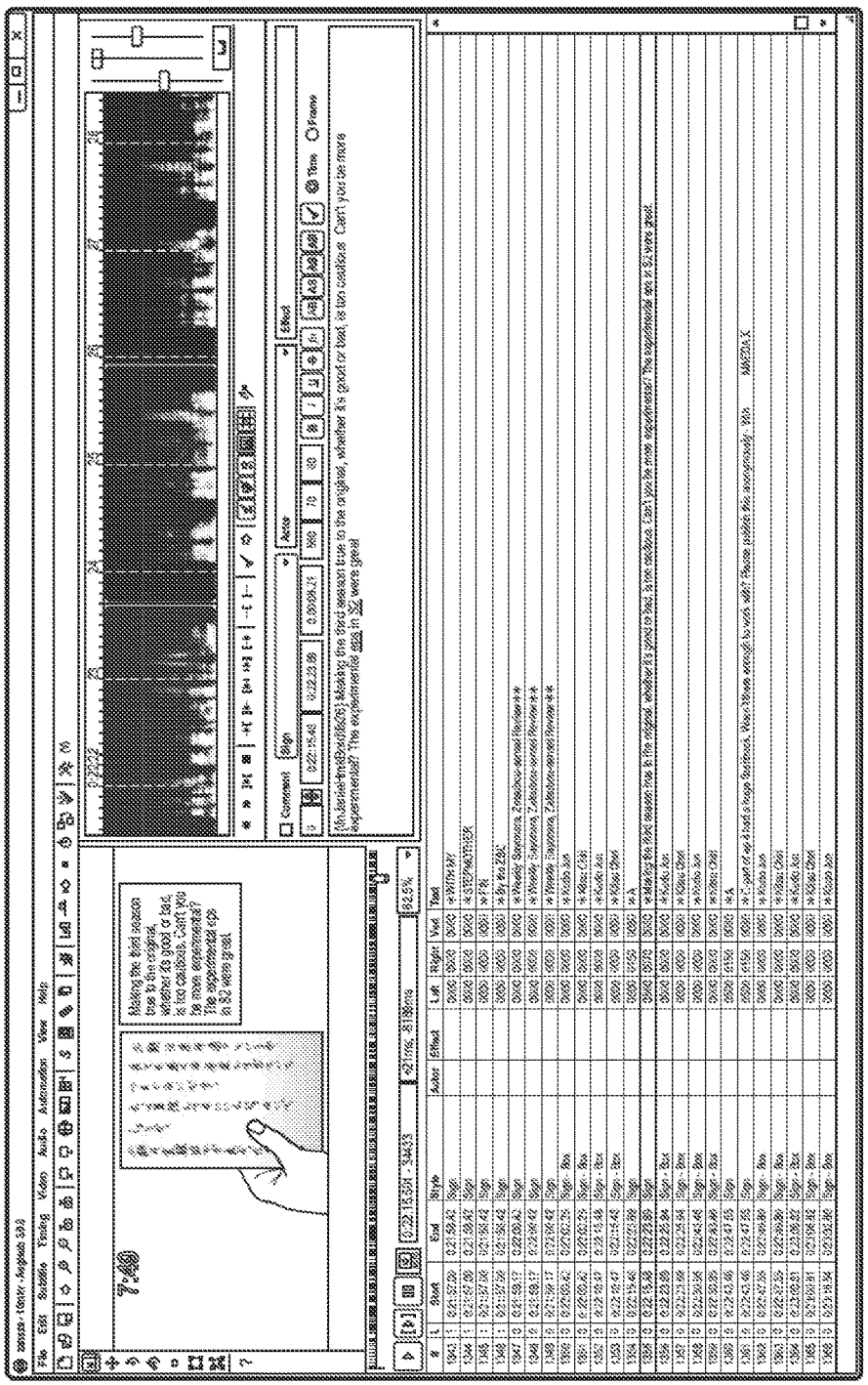
FIG. 1 is a screen shot of Aegisub (http://www.aegisub.org/), a free open-source tool for creating and modifying subtitles to audio.

A key component of the system is the use of a subtitle editing program. A preferred program is known as Aegisub™ (http://www.aegisub.org/) developed by N. Hansen and R. Monteiro. Aegisub™ is a free, open-source, cross-platform, subtitle editing program. It is extensively used in what is known as "fansubbing," the practice of creating or translating unofficial, noncommercial subtitles for visual media by fans. The software is considered the standard in fansubbing, and has been recommended in the online "Guide to Fansubbing." FIG. 1 illustrates an Aegisub user interface.

The disclosed system does not use this program tool to edit information. Rather, it is used to correlate a relation between time code sequences and text contexts. The Aegisub interface of FIG. 1 consists of three sections. In a top left section, a particular text content and its location in time code sequence (similar to progress bar) are shown. In a top right section, in addition to the word content, start and end time code sequence and the content location in a word document—e.g., start from left, end at right, and which line—is shown. In the bottom section, a table is shown where start and end time code sequences are associated with an audio block, as well as the location of text content in the word document (e.g., left, right, the line number).

For example, in line #1355 (FIG. 1), the text content reads "Making the third season true to the original . . . " and has its location at the original word document (0560, 0070, 0080). The line entry also carries the time code sequences representing the audio block. All information regarding to "Making the third season true to the original . . . " has been built in one line with a table index of 1355. Using the same steps, an entire document can be edited and similarly presented in a table as shown in FIG. 1.

Figures 2, 3:
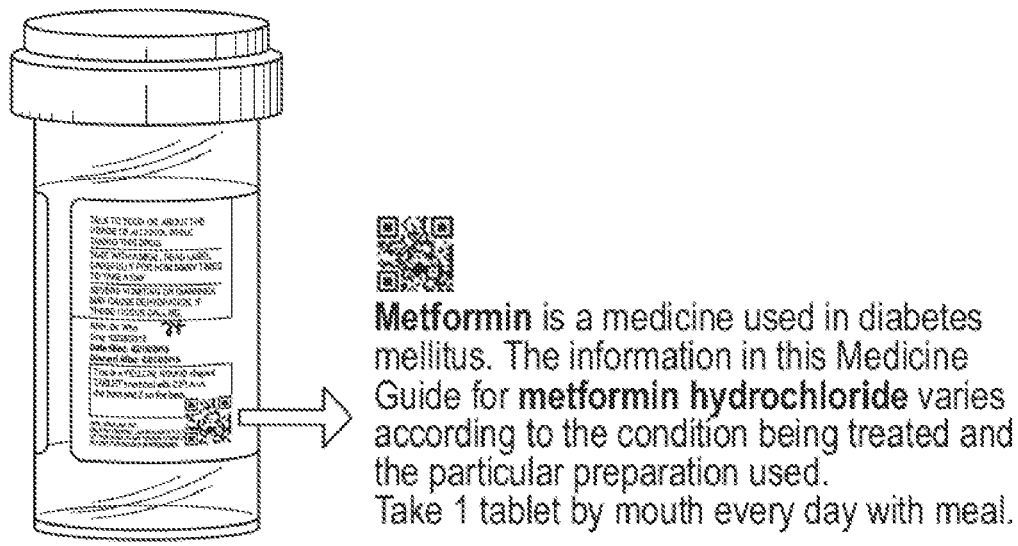
FIG. 2 illustrates an example of URL links generated by an embodiment of the present system and method.
FIG. 3 illustrates an example medicine bottle with a barcode label in accordance with an embodiment of the present system and method.

FIG. 2 is an example of URL links generated by the present system. The URL includes hypertext transfer protocol (http) [1], a website address that refers to the host name and website server [2], a component that allows users to hear audio in the website [3], and an unique index code [4] that is generated and associated with a piece of audio clip (time segment) stored in a database.

FIG. 3 is an example of a preferred use, showing a 2D barcode as part of the "instructions for use" label on a bottle of medicine. As previously noted, medicine bottles usually have very limited space to carry information about the prescription, including pill count, limitations, side effects, dosage, and other critical information. As a result, the detail is often in small print and very hard to read. Placing a 2D barcode on the label to provide an audio signal to announce the selected information is very useful, especially to those who need glasses to assist reading.

FIG. 4 is one example of the table in which the texts in the document are segmented according to their meaning and associated with their audio time sequences. Details are as follows:

POT—Point of Text is the entry point of URL index code. It points the text corresponding to an audio segment to the website server that a user uses to hear audio;

TL—Text lines carry number of text rows to be combined (since audio signal is continued). Text document is segmented according to meaning and placed in sequential rows. Each row represents the resolution of an audio signal for the text segment. It can be index by a single row or by combination of a number of rows continuously;

Start and End—Represent audio segmentation indices corresponding to text contents placed in this row;

L_Left and L_Vert —Represent the start location of the text in the document (left char, line num). It assumes the document associated with the audio is in one page;

R_Left and R_Vert—Represent the end location of the text in the document (last char, line num). It also assumes the document associated with the audio is one page; and English—This shows the text segment or an independent sentence that is stored. In this case, the content is in the English language. The content can be independent of language or it can be any language associated with the audio (audio and text may be in different languages with the same meaning).

Figure 5:
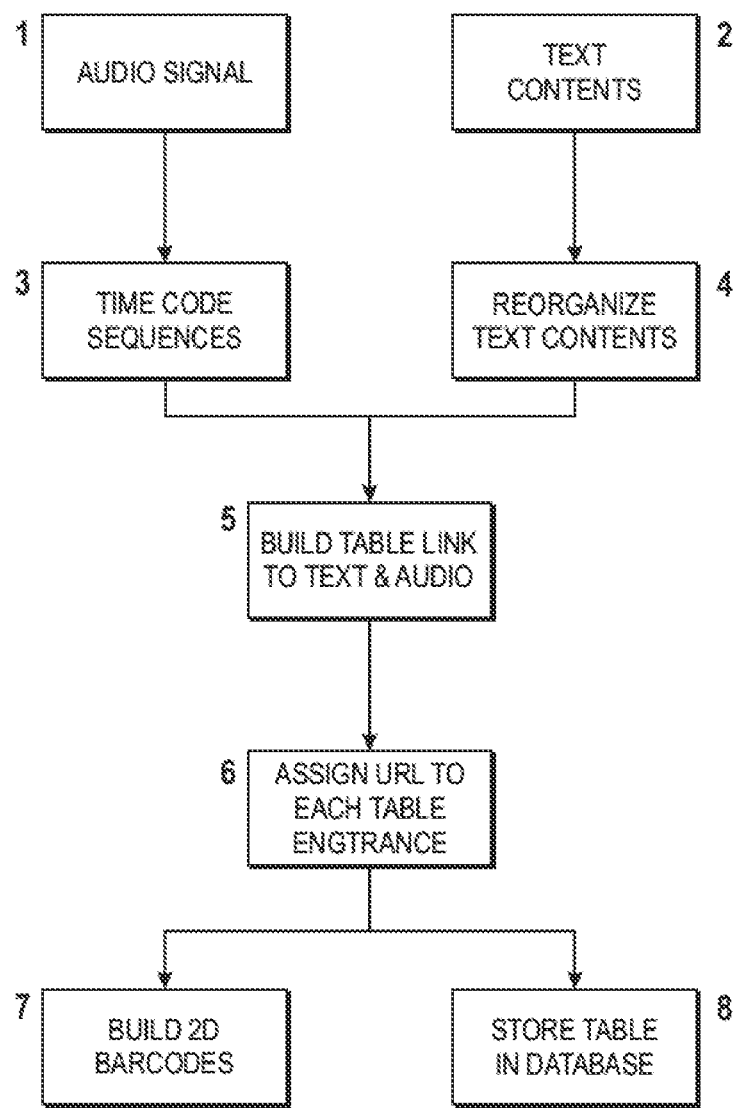
FIG. 5 is a flow chart of an exemplary embodiment of the disclosed system and method.

FIG. 5 is a flow chart illustrating a preferred method sequencing the general steps for constructing an embodiment of the disclosed system. As shown, the eight-step process proceeds as follows:

Step 1: Recording Audio signal (or generate audio using computer text-to-speech software);

Step 2: Associating the original word document with audio. It can be an article, description, and/or list of instructions, etc.;

Step 3: Generating time code sequences for entire audio signal;

Step 4: Editing the word document according to meaning and subjecting to text content segment blocks;

Step 5: Building a table. Each table carries a subject of text content. There are elements addressing start and end time code sequence of this subject context, also addresses the location indices in its word document;

Step 6: Assigning each row a URL;

Step 7: Building a 2D barcode to carry the URL; and

Step 8: Storing the table onto a Cloud database as a head of audio and text document.

Digital recorded audio signal can be precisely located and segmented by time code sequences through a time code generator. Time code looks like HOURS:MINUTES:SECONDS (00:00:00). The HOURS are number between 00 to 23 hours, the MINUTES field ranges from 00 through 59 minutes, and the SECONDS field likewise ranges from 00 through 59 seconds. The corresponding text can be stored in the memory in a format which can be indexed by the time code sequences. For example, the following recorded audio signal can be addressed by time code sequences as start at 0:22:15 and end at 0:22:29:

Metformin is a medicine used in diabetes mellitus. The information in this Medicine Guide for metformin hydrochloride varies according to the condition being treated and the particular preparation used. Take 1 tablet by mouth every day with meal With properly formatted text to match the Time code sequence, one is able to know the start and end time code sequences based on the text used. Placement of a 2D barcode, in which a URL points to text content stored in the memory, proximate the printed text on the label, possibly with some indicia (e.g., an arrow) to convey the association between the printed text and the barcode, is useful. An Internet device, such as a medical pendant, smartphone, etc., which has the ability to scan 2D barcodes, can be used to scan the barcode and send the URL to a Cloud-based computing platform. Based on the text content link, the computer can obtain time code sequences. With the time code sequences, a block of audio signal is extracted and transferred back to the Internet device and, via an audio capability, the instructions are announced to the user of the device.

In order to effectively sort continuous audio signals, the text content is edited and grouped in a table format based on meaning or in paragraphs. Then, the associated audio file with subject audio segments is correspondingly edited to be defined by time code sequences. Finally, the time code sequences are associated with corresponding text content block and placed in the table illustrated in FIG. 4. This builds the link between static text content and continuous audio signal. This process is known as "editing."

Since the URL points to the start point of a selected word content block as Point of Text (POT) in the first column in FIG. 4, it links to a corresponding audio segment. With the URL, audio signal representing the text contents can be extracted according to the Total Lines (TL) listed in the second column of FIG. 4. This number indicates how many time periods or how many rows will be added and extracted. After the editing process, a table is built and releases a group of URLs which link text content and audio signals. It is important to have audio start and end time code sequences to identify the audio segment. The audio signal itself can be recorded by a human or generated by computer software, such as Text-to-Speech, according to the text contents. While used in the description above, actually generating audio signals from text contents is not an objective in the present system or methods. However, such audio generation is well-within the knowledge and ability of those skilled in the relevant art.

The matter set forth in the foregoing description and accompanying drawings is offered by way of illustration only and not as a limitation. While particular embodiments have been shown and described, it will be apparent to those skilled in the art that changes and modifications may be made without departing from the broader aspects of applicant's contribution. The actual scope of the protection sought is intended to be defined in the following claims when viewed in their proper perspective based on the prior art.

What is claimed is:

1. A method for providing an audio signal to an electronic device via an Internet connection where the audio signal is related to printed information associated with a bar code, the method comprising the steps of:

creating text content based on the printed information;

recording an audio signal in a first language based on the printed information in a second language;

editing the text content into text segments based on meaning;

listing the text segments in a table;

defining audio segments of the audio signal by start and stop time code sequences of the recording, wherein the audio segments correspond with listed text segments in the table;

adding the time code sequences to the table for the text segment based on the corresponding audio segment;

adding a location to the table for each text segment in the text content;

storing the audio signal and text segments in table format on a cloud-based server; and generating a unique URL linked to the stored audio signal and text segments and to a web-based audio play application;

generating a barcode containing the URL; and scanning the barcode to activate the audio signal.

2. The method according to claim 1, wherein the first language and the second language are different languages.

3. The method according to claim 1, further comprising the step of generating a plurality of audio signals, wherein each audio signal is in a language different than the others, including the second language.

4. The method according to claim 3, further comprising the step of selecting one of the plurality of audio signals to have defined audio segments.

5. The method according to claim 1, further comprising the step of generating a plurality of audio signals, wherein each audio signal is in a language different than the others, not including the second language.

6. The method according to claim 5, further comprising the step of selecting one of the plurality of audio signals to have defined audio segments.

7. The method according to claim 1, wherein the step of scanning is performed by a mobile, internet device with a communication protocol.

8. The method according to claim 1, further comprising affixing the barcode to a medicine container wherein the printed information comprises instructions for use of a drug.

9. The method according to claim 1, further comprising affixing the barcode to a product container wherein the printed information comprises instructions for use of the product.

* * * * *